(12) United States Patent
Goshayeshgar (10) Patent No.: US 9,282,988 B2
(45) Date of Patent: Mar. 15, 2016

(54) FORMED DEPLOYABLE SUPERELASTIC BLADE AND METHOD OF USE

(71) Applicant: KYPHON SARL, Neuchatel (CH)

(72) Inventor: Mojan Goshayeshgar, Atherton, CA (US)

(73) Assignee: KYPHON SÀRL, Neuchâtel (CH)

( * ) Notice: Subject to any disclaimer, the term of this patent is extended or adjusted under 35 U.S.C. 154(b) by 208 days.

(21) Appl. No.: 13/804,473

(22) Filed: Mar. 14, 2013

(65) Prior Publication Data

US 2014/0276729 A1    Sep. 18, 2014

(51) Int. Cl.
*A61B 17/32*    (2006.01)
*A61B 18/14*    (2006.01)
*A61B 17/00*    (2006.01)
*A61B 18/00*    (2006.01)

(52) U.S. Cl.
CPC ....... *A61B 17/320016* (2013.01); *A61B 18/148* (2013.01); *A61B 2017/00331* (2013.01); *A61B 2018/00196* (2013.01); *A61B 2018/00434* (2013.01); *A61B 2018/1475* (2013.01); *A61B 2218/002* (2013.01); *A61B 2218/007* (2013.01)

(58) Field of Classification Search
CPC .............................................. A61B 17/320016
USPC ......................................................... 606/79
See application file for complete search history.

(56) References Cited

U.S. PATENT DOCUMENTS

| 6,979,332 | B2 | 12/2005 | Adams |
| 7,918,849 | B2 | 4/2011 | Bleich et al. |
| 8,123,750 | B2 * | 2/2012 | Norton et al. .................. 606/80 |
| 2002/0183758 | A1 * | 12/2002 | Middleton et al. ............. 606/79 |
| 2006/0258951 | A1 | 11/2006 | Bleich et al. |
| 2008/0033465 | A1 * | 2/2008 | Schmitz et al. ............... 606/170 |
| 2008/0114364 | A1 * | 5/2008 | Goldin et al. ................... 606/79 |
| 2008/0161809 | A1 * | 7/2008 | Schmitz et al. ................. 606/79 |
| 2009/0204119 | A1 | 8/2009 | Bleich et al. |
| 2013/0012933 | A1 | 1/2013 | Pellegrino et al. |
| 2013/0197551 | A1 * | 8/2013 | Yoon et al. .................... 606/170 |

* cited by examiner

*Primary Examiner* — Carl H Layno
*Assistant Examiner* — Jennifer Ghand
(74) *Attorney, Agent, or Firm* — Martin & Ferraro LLP (57) ABSTRACT

A device includes an outer member extending along a longitudinal axis between a first end and a second end. The first end includes an opening. The outer member includes an inner surface defining a first passageway that is in communication with the opening. An inner member is movably disposed in the first passageway. The inner member includes an inner surface defining a second passageway. The inner member further includes a first end including a cutting tip. The inner member is movable between a first orientation in which the cutting tip is disposed within the first passageway and the inner member has a linear configuration and a second orientation in which the cutting tip extends through the opening and the inner member has an arcuate configuration. Methods of use are provided.

24 Claims, 3 Drawing Sheets

FORMED DEPLOYABLE SUPERELASTIC BLADE AND METHOD OF USE

TECHNICAL FIELD

The present disclosure generally relates to medical devices for the treatment of musculoskeletal structures, and more particularly to a surgical system and method employing a formed deployable superelastic blade to debulk a hypertrophied ligamentum flavum.

BACKGROUND

Spinal stenosis typically occurs when the spinal cord, cauda equina and/or nerve root(s) are impinged by one or more tissues in the spine, such as a buckled or thickened ligamentum flavum. Impingement of neural and/or neurovascular tissue in the spine by a buckled or thickened ligamentum flavum may cause pain, numbness and/or loss of strength or mobility in one or both of a patient's lower limbs and/or of the patient's back.

In lumbar spinal stenosis (LSS), space around the spinal cord becomes narrow, thus compressing the spinal cord and the nerve roots. This causes back pain with neurogenic claudication, i.e., pain, numbness, or weakness in the legs that worsens with standing or walking and is alleviated with sitting or leaning forward. Compression of neural elements generally occurs as a result of ligamentum flavum hypertrophy. LSS is one of the most common reasons for back surgery and the most common reason for lumbar spine surgery in adults over 65 years of age. Patients suffering from spinal stenosis are typically first treated with conservative approaches such as exercise therapy, analgesics, anti-inflammatory medications, and epidural steroid injections. When these conservative treatment options fail and symptoms are severe, surgery may be required to remove impinging tissue and decompress the impinged nerve tissue.

Decompressive laminectomy, a well-known treatment for LSS, unroofs the spinal canal by resectioning posterior spinal elements, such as the ligamentum flavum. Wide muscular dissection and retraction is needed to achieve adequate surgical visualization. The extensive resection and injury to the posterior spine and supporting muscles can lead to instability with significant morbidity, both post-operatively and longer-term. Spinal fusion may be required to reduce the resultant instability. Laminectomy may be used for extensive multilevel decompression.

A combination of hemilaminotomy and laminotomy, often referred to as laminoforaminotomy, is less invasive than laminectomy. This procedure focuses on the interlaminar space in order to minimize resectioning of the stabilizing posterior spine. Generally, laminotomy removes the ligamentum flavuum. Muscular dissection and retraction are required to achieve adequate surgical visualization.

Microendoscopic decompressive laminotomy (MEDL) is somewhat similar to laminotomy, but utilizes endoscopic visualization. The position of a tubular working channel is confirmed by fluoroscopic guidance, and serial dilators (METRx™ lumbar endoscopic system, Medtronic) are used to dilate the musculature and expand the fascia. For MEDL, an endoscopic curette, rongeur, and drill are used for the laminotomy, facetectomy, and foraminotomy. The working channel may be repositioned from a single incision for multilevel and bilateral dissections.

Minimally invasive procedures in nerve and/or soft tissue such as the spine or the breast, however, are difficult to perform using standard scissors and scalpel. Therefore, methods of cutting tissue may include using a scalpel and scissors or electrosurgical procedures using radio frequency (RF) energy. Electrosurgical procedures and techniques using radio frequency energy are currently used since they generally reduce patient bleeding and trauma associated with cutting operations.

Radio frequency energy controls bleeding by coagulating small blood vessels. Another method of controlling bleeding is through the use of heat. For example, some commercially available scalpels use direct heat to control bleeding. However, while the bleeding is generally controlled, the cutting of tissue is often slower than with radio frequency energy and the knife edge readily dulls. Other commercially available scalpels use ultrasonic energy generally at 50 kHz to heat the tissue so as to coagulate severed blood vessels but cut slower than a standard electrosurgical electrode and are costly as a custom ultrasonic generator is required.

Radiofrequency energy is used in a wide range of surgical procedures because it provides efficient tissue resection and coagulation and relatively easy access to the target tissues through a portal or cannula. Conventional monopolar high frequency electrosurgical devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Present electrosurgical techniques used for tissue ablation may suffer from an inability to provide the ability for fine dissection of soft tissue. The distal end of electrosurgical devices is wide and flat, creating a relatively wide area of volumetric tissue removal and making fine dissections along tissue planes more difficult to achieve because of the lack of precision provided by the current tip geometries.

In addition, identification of the plane is more difficult because the large ablated area and overall size of the device tip obscures the physician's view of the surgical field. The inability to provide for fine dissection of soft tissue is a significant disadvantage in using electrosurgical techniques for tissue ablation, particularly in arthroscopic, otolaryngological, and spinal procedures. This disclosure describes an improvement over these prior art technologies.

SUMMARY

Accordingly, a surgical system and method employing a formed deployable superelastic blade to debulk a hypertrophied ligamentum flavum are provided. In one embodiment, in accordance with the principles of the present disclosure, the surgical system includes a device for performing a surgical procedure. The device comprises an outer member extending along a longitudinal axis between a first end and a second end. The first end includes an opening. The outer member includes an inner surface defining a first passageway that is in communication with the opening. An inner member is movably disposed in the first passageway. The inner member includes an inner surface defining a second passageway. The inner member further includes a first end including a cutting tip. The inner member is movable between a first orientation in which the cutting tip is disposed within the first passageway and the inner member has a linear configuration and a second orientation in which the cutting tip extends through the opening and the inner member has an arcuate configuration.

In one embodiment, in accordance with the principles of the present disclosure, the surgical system includes an outer member extending along a longitudinal axis between a first end and a second end. The first end includes a circular opening extending parallel to the longitudinal axis. The outer member includes an inner surface defining a first passageway that is in communication with the opening. The first passageway extends parallel to the longitudinal axis and has a uniform diameter. A stylet is removably disposed in the passageway. The stylet includes a blunt tip that extends through the opening configured to create an access path to a selected portion of a patient's anatomy. An inner member comprising a super elastic metal is movably disposed in the first passageway after the stylet is removed from the first passageway. The inner member includes an inner surface defining a second passageway. The inner member further includes a first end includes a cutting tip having an aperture including a first portion extending parallel to the longitudinal axis and a second portion extending perpendicular to the longitudinal axis. The aperture defines a scoop portion of the cutting tip. The inner member includes at least one electrode positioned adjacent the aperture configured to emit radio frequency (RF) energy to destruct tissue and/or nerves. A second end of the inner member is coupled to a suction source to provide suction through the opening and into the second passageway. The second end of the inner member is also coupled to an irrigation source to deliver irrigation fluid through the second passageway and the opening. The inner member is movable between a first orientation in which the cutting tip is disposed within the first passageway and the inner member has a linear configuration and a second orientation in which cutting tip extends through the opening and the inner member has an arcuate configuration.

In one embodiment, in accordance with the principles of the present disclosure, a method for correction of a bone injury is provided. The method comprises the steps of: providing a device comprising: an outer member extending along a longitudinal axis between a first end and a second end, the first end including an opening, the outer member including an inner surface defining a first passageway that is in communication with the opening, and a stylet removably disposed in the passageway, the stylet including a blunt tip that extends through the opening; inserting the stylet through an incision and translating the stylet into the anatomy of a patient such that the stylet creates an access path to a selected portion of the patient's anatomy; removing the stylet from the first passageway; inserting an inner member into the first passageway, the inner member including an inner surface defining a second passageway, the inner member further including a first end including a cutting tip; translating the inner member between a first orientation in which the cutting tip is disposed within the first passageway and the inner member has a linear configuration and a second orientation in which the cutting tip extends through the opening and the inner member has an arcuate configuration; and applying mechanical force to the inner member such that the cutting tip cuts through the selected portion of the patient's anatomy.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system and method for bone repair. It is envisioned that the surgical system and method may be employed in applications such as for correction of lumbar spinal stenosis. For example, the surgical system and method can include a formed deployable superelastic blade to debulk a hypertrophied ligamentum flavum in lumbar spinal stenosis. In one embodiment, the system includes a nested cannula and blunt stylet access the ligamentum flavum through interlaminar space. After access to the ligamentum flavum is achieved, the stylet is removed from the cannula and a curved super-elastic metal tube comprising Nitinol is inserted through the cannula. The tube has a cutting tip and is formed to cut through the ligamentum flavum at a thickness of less than 1.5 mm in each deployment. In some embodiments, the cutting tip is energized with radio frequency (RF) energy to reduce the amount of mechanical force required to cut through the ligamentum flavum. In some embodiments, the tube is coupled to a suction source to provide suction through the tube. In some embodiments, the tube is coupled to an irrigation source to deliver irrigation fluid through the tube.

It is contemplated that one or all of the components of the surgical system may be disposable, peel-pack, pre-packed sterile devices. One or all of the components of the surgical system may be reusable. The surgical system may be configured as a kit with multiple sized and configured components that are preformed to have different sizes and shapes.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employs various surgical approaches to the spine, including anterior, posterior, posterior mid-line, direct lateral, postero-lateral, and/or antero-lateral approaches, and in other body regions. The present disclosure may be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system for treating spinal disorders such as, for example, stenosis that includes a formed deployable superelastic blade to debulk a hypertrophied ligamentum flavum. The disclosure also includes a description of related methods of employing the formed deployable superelastic blade. Alternate embodiments are also disclosed. Reference will now be made in detail to the exemplary embodiments of the present disclosure, which are illustrated in the accompanying figures. Turning now to FIGS. 1-4, there are illustrated components of a surgical system, such as, for example, a surgical system 30 and embodiments in accordance with the principles of the present disclosure.

The components of system 30 can be fabricated from biologically acceptable materials suitable for medical applications, including metals, synthetic polymers, ceramics and bone material and/or their composites, depending on the particular application and/or preference of a medical practitioner. For example, the components of system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of balloon system 20 may have material composites, including the above materials, to achieve various desired characteristics such as strength, rigidity, elasticity, compliance, biomechanical performance, durability and radiolucency or imaging preference. The components of system 30, individually or collectively, may also be fabricated from a heterogeneous material such as a combination of two or more of the above-described materials. The components of system 30 may be monolithically formed, integrally connected or include fastening elements and/or instruments, as described herein.

System 30 is employed, for example, with an open, mini-open or minimally invasive surgical technique to debulk a hypertrophied ligamentum flavum. System 30 includes an outer member, such as for example, a cannula 32 extending along a longitudinal axis B between a first end including a first end surface 34 and a second end including a second end surface 36. Surfaces 34, 36 are planar and extend perpendicular to axis B. It is envisioned that surface 34 and/or surface 36 may be variously configured and dimensioned, such as, for example, planar, concave, polygonal, irregular, uniform, non-uniform, staggered, tapered, consistent or variable, depending on the requirements of a particular application. It is further envisioned that surface 34 and/or surface 36 may be disposed at alternate orientations, relative to axis B, such as, for example, transverse, perpendicular and/or other angular orientations relative to axis B such as acute or obtuse, and/or may be offset or staggered, depending on the requirements of a particular application.

The first end of cannula 32 includes a circular first opening 38 extending parallel to axis B through surface 34 and the second end of cannula 32 includes a circular second opening 40 extending parallel to axis B through surface 36. Cannula 32 includes an inner surface 42 defining a first passageway 44 that is in communication with openings 38, 40. Passageway 44 extends parallel to axis B between surfaces 34, 36. Passageway 44 has a length defined by the distance between surfaces 34, 36. Passageway 44 has a cylindrical configuration defining a uniform diameter along the length of passageway 44. It is envisioned that all or only a portion of opening 38, opening 40 and/or passageway 44 may be variously configured and dimensioned, such as, for example, oval, oblong, square, polygonal, irregular, uniform, non-uniform, offset, staggered, tapered, consistent or variable, depending on the requirements of a particular application. It is further envisioned that opening 38, opening 40 and/or passageway 44 may be disposed at alternate orientations, relative to axis B, such as, for example, transverse, perpendicular and/or other angular orientations relative to axis B such as acute or obtuse, and/or may be offset or staggered, depending on the requirements of a particular application.

Figure 4:
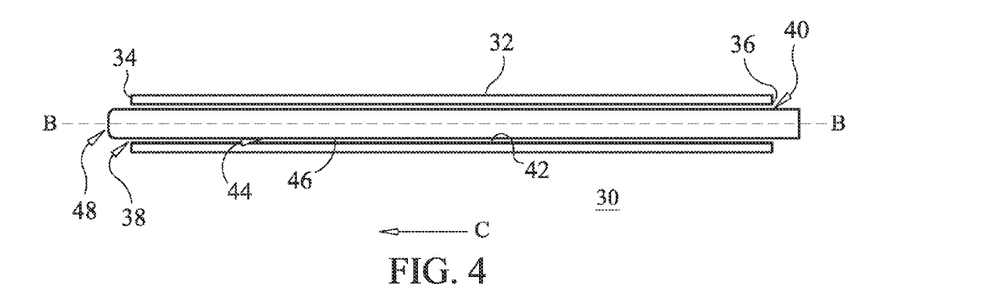
FIG. 4 is a side, cross sectional view of one embodiment the system shown in FIG. 1 in accordance with the principles of the present disclosure.

A surgical instrument, such as, for example, a stylet 46 is removably disposed in passageway 44, as shown in FIG. 4. Stylet 46 has a length that is greater than the length of cannula 32 such that a first end of stylet 46 extends through opening 38 and a second end of stylet 46 extends through opening 40 when stylet 46 is disposed in passageway 44. The first end of stylet 46 comprises a tip 48 which can be blunt or sharpened. In some embodiments, stylet 46 is cannulated to accommodate a guide wire of a spinal needle assembly. Stylet 46 may be made of any appropriate medical grade material, such as, for example, stainless steel. Stylet 46 is configured to push and/or cut a tunnel or access path through soft tissue and bone to permit placement of a surgical instrument, such as, for example, an inner member 50 into a desired interior body region of a patient, such as, for example, a region adjacent the ligamentum flavum of the patient. After stylet 46 creates the tunnel or access path to the ligamentum flavum, stylet 46 may be removed from passageway 44.

Member 50 comprises a super elastic metal, such as, for example, Nitinol and is movably disposed in passageway 44 after stylet 46 is removed from passageway 44. That is, member 50 and stylet 46 are not disposed in passageway 44 simultaneously. Member 50 includes an inner surface 52 defining a second passageway 54. A first end of member 50 includes an aperture 56 extending through a first end surface 56 of member 50. The first end of member 50 includes a cutting tip defined by aperture 56 having a first portion extending parallel to the longitudinal axis and a second portion extending perpendicular to the longitudinal axis so as to define a scoop portion. The cutting tip is configured to cut through a ligamentum flavum of a patient at a thickness less than about 1.5 mm. A second end of member 50 includes a circular opening 60 extending parallel to axis B through a second end surface 62 of member 50.

Passageway 54 is in communication with aperture 56 and opening 60. Passageway 54 extends parallel to axis B between surfaces 58, 62. Passageway 54 has a length defined by the distance between surfaces 58, 62. Passageway 54 has a cylindrical configuration defining a uniform diameter along the length of passageway 54. It is envisioned that all or only a portion of aperture 56, opening 60 and/or passageway 54 may be variously configured and dimensioned, such as, for example, oval, oblong, square, polygonal, irregular, uniform, non-uniform, offset, staggered, tapered, consistent or variable, depending on the requirements of a particular application. It is further envisioned that aperture 56, opening 60 and/or passageway 54 may be disposed at alternate orientations, relative to axis B, such as, for example, transverse, perpendicular and/or other angular orientations relative to axis B such as acute or obtuse, and/or may be offset or staggered, depending on the requirements of a particular application.

Figure 3:
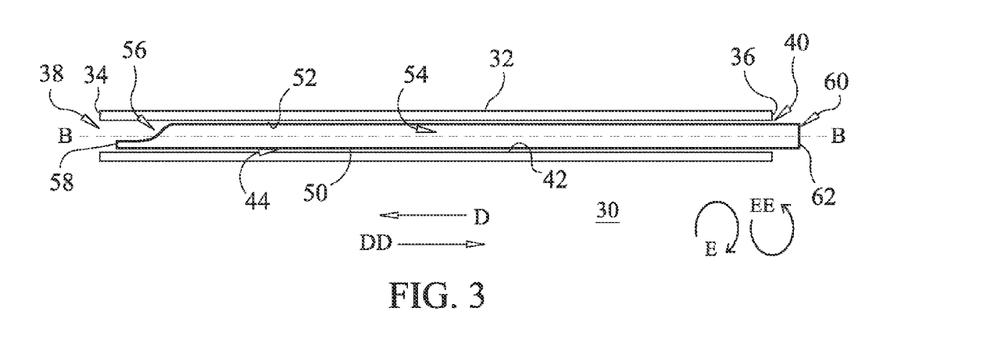
FIG. 3 is a side, cross sectional view of the system shown in FIG. 1.

Member 50 includes at least one electrode 64 positioned adjacent aperture 56 configured to emit radio frequency (RF) energy to cut and/or destroy tissue and/or nerves. It is envisioned that member 50 may include one or a plurality of electrodes 54. As shown in FIG. 3, member includes three electrodes 64. One electrode 64 is disposed in or on a first sidewall that extends parallel to an axis defined by member 50, one electrode is disposed in or on a second sidewall that extends parallel to the axis defined by member 50 and a third electrode is disposed in or on a third sidewall that extends perpendicular to the axis defined by member 50. That is, two electrodes 64 are positioned to parallel to one another, and the third electrode 64 is perpendicular to the two parallel electrodes 64. It is envisioned that electrodes 64 can be disposed inside, outside or within the thickness of the respective sidewall. It is further envisioned that electrodes 64 can be straight, helical, curved symmetrical, or asymmetrical and positioned symmetrically or directionally.

In some embodiments, electrodes 64 are configured to be energized by monopolar RF. In some embodiments, electrodes 64 are configured to be energized by bipolar RF. In one embodiment, the PEAK PlasmaBlade™ is used to cut and/or destroy tissue and/or nerves. The PEAK PlasmaBlade™ device receives RF energy in short pulses via a highly insulated cutting electrode, so it cuts at a much lower average temperature than conventional electrosurgery. Due to its lower temperatures, PEAK PlasmaBlade™ technology doesn't cause the extensive collateral tissue damage that can be associated with traditional electrosurgery tools. This is important because of the small temperature difference between the temperature required for cutting or destroying tissue and the temperature normally injurious to healthy tissue, a known heating pattern and precise temperature control is needed to lead to more predictable temperature distribution to cut or destroy selected tissue while minimizing the damage to surrounding tissue. Excessive temperatures can cause adverse tissue effects. During the course of heating, tissue in an overly-heated area may become desiccated and charred. As tissue temperature increases to 100° C., tissue will lose water content due to evaporation or by the diffusion of liquid water from treated cells, and the tissue becomes desiccated. This desiccation of the tissue changes the electrical and other material properties of the tissue, and may impede treatment. For example, as the tissue is desiccated, the electrical resistance of the tissue increases, making it increasingly more difficult to supply power to the tissue. At tissue temperatures in excess of 100° C., the solid contents of the tissue begin to char. Like desiccated tissue, charred tissue is relatively high in resistance to current and may impede treatment. Accordingly, in some embodiments, system 30 includes a temperature or impedance-based feedback system to enable system 30 to accurately monitor the extent of tissue desiccation and permit continued delivery of the RF energy.

Figure 5A:
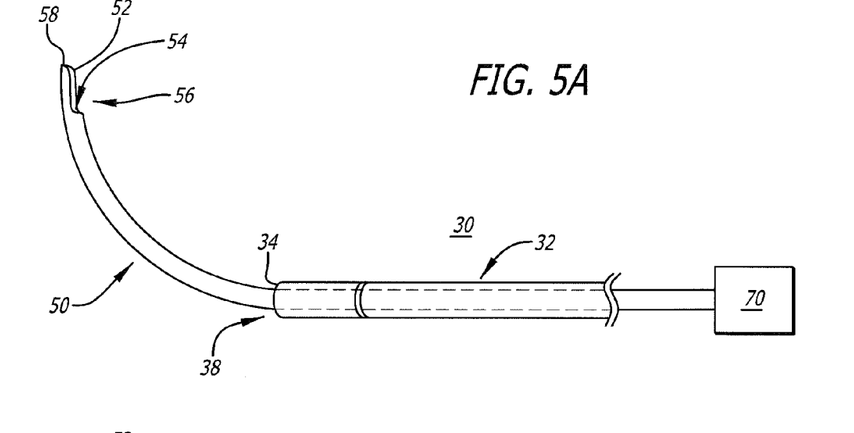
FIG. 5A is a breakaway side view of another embodiment of a surgical system in accordance with the invention.
Figure 5B:
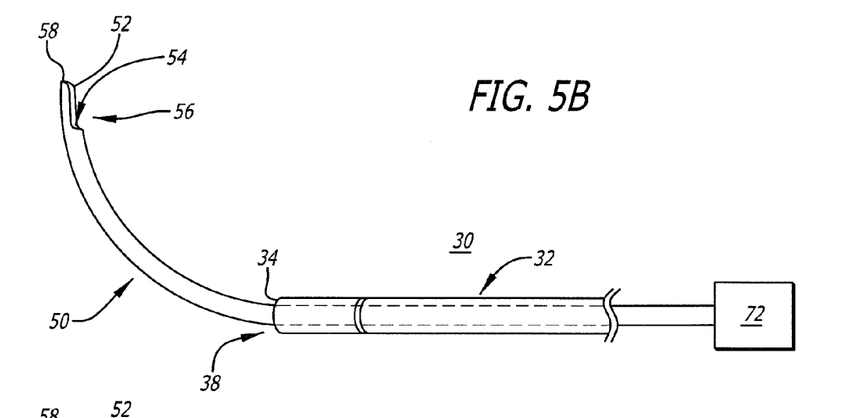
FIG. 5B is a breakaway side view of another embodiment of a surgical system in accordance with the invention.
Figure 5C:
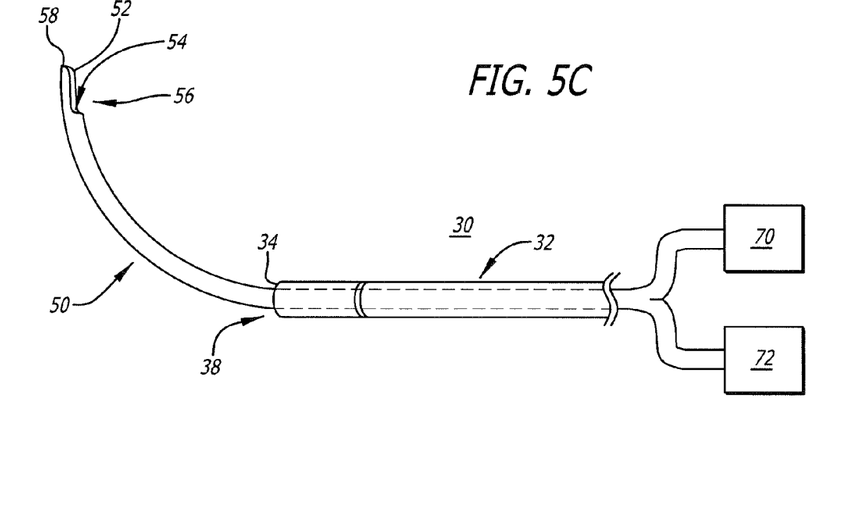
FIG. 5C is a breakaway side view of another embodiment of a surgical system in accordance with the invention; and Like reference numerals indicate similar parts throughout the figures.

In some embodiments, as depicted in FIG. 5A, the second end of member 50 is coupled to a suction source 70, such as, for example, a vacuum to provide suction through aperture 56 and into passageway 58 to remove tissue and/or other debris adjacent a surgical site, such as, for example, the ligamentum-flavum of the patient, such that the tissue and/or other debris is removed from the surgical site and is disposed in passageway 58. In some embodiments, as depicted in FIG. 5B, the second end of member 50 is coupled to an irrigation source 72 to deliver irrigation fluid through passageway 50 and aperture 56 such that the irrigation fluid may be delivered to a location adjacent a surgical site, such as, for example, the ligamentum-flavum of the patient. It is envisioned that the irrigation fluid may also be delivered through passageway 50 and aperture 56 such that the irrigation fluid can cool electrodes 64. In some embodiments, as depicted in FIG. 5C, the second end of member 50 is coupled to the suction source 70 and the irrigation source 72 simultaneously.

Figure 1:
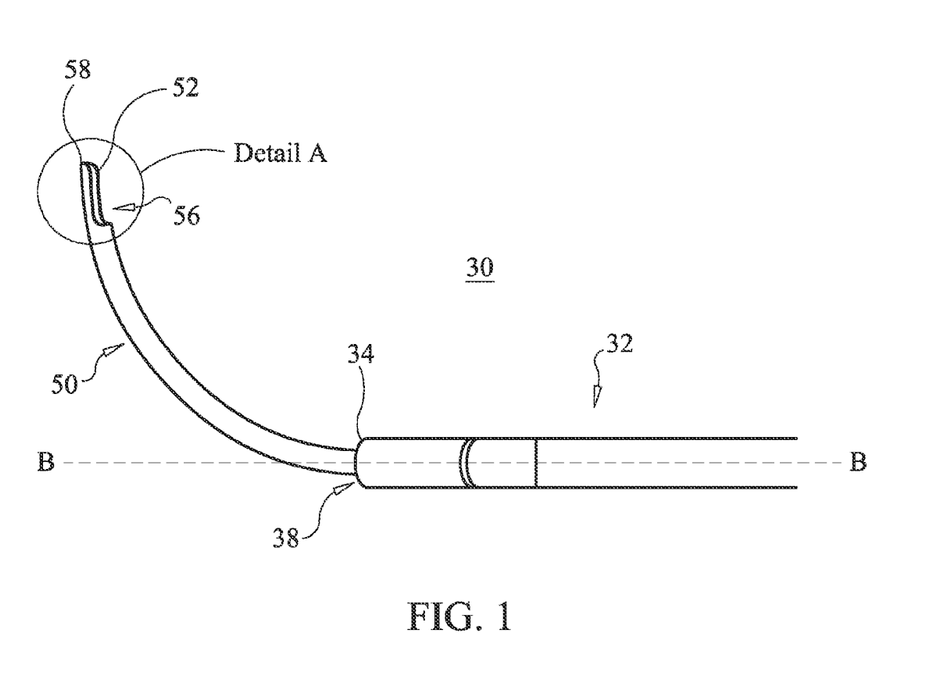
FIG. 1 is a breakaway, side view of one embodiment of a surgical system in accordance with the principles of the present disclosure.
Figure 2:
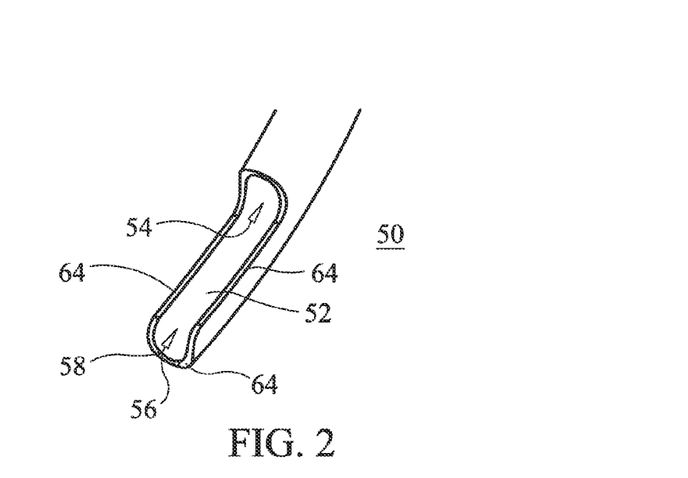
FIG. 2 is a close up, proximal view of a component of Detail A shown in FIG. 1.

Member 50 is movable between a first orientation in which the surface 58 of member 50 is disposed within passageway 44 and member 50 has a linear configuration, as shown in FIG. 4, and a second orientation in which the surface 58 of member 50 extends through 38 and member 50 has an arcuate configuration, as shown in FIG. 1. Because member 50 is made of a super elastic metal, member 50 will have the linear configuration shown in FIG. 4 when member 50 is moved relative to cannula 32 such that surface 58 of member 50 is disposed in passageway 44. That is, member 50 moves from the second orientation to the first orientation by translating member 50 relative to cannula such that surface 58 of member 50 is disposed in passageway 44. Member 50 is preformed to have the curvature shown in FIG. 1 such that aperture 56 may be positioned adjacent a hypertrophied ligamentum flavum without the need to remove the lamina and/or one or more facet joints. The amount of curvature may therefore be selected depending upon the requirements of a particular application. In some embodiments, system 30 includes a plurality of members 50, each being preformed to have a different curvature. It is envisioned that such members 50 may be part of a kit.

In assembly, operation and use, system 30 is employed with a surgical procedure, such as, for a correction or treatment of bone fractures. It is contemplated that one or all of the components of system 30 can be delivered or implanted as a pre-assembled device or can be assembled in situ. System 30 may be completely or partially revised, removed or replaced. For example, system 30 can be employed with a surgical correction treatment of an applicable condition or injury of an affected portion of a patient, such as, for example, a hypertrophied ligamentum flavum. It is envisioned that system 30 may also be used to treat other affected portions of the patient, such as, for example, a hypertrophied facet joint, osteophytes (bone spurs) on vertebrae, facet joint synovial cysts, a collapsed, bulging or herniated intervertebral disc, a calcaneus bone, bones of the feet or hands, bones of the spine, bones of the arms and legs, etc.

In use, to treat a hypertrophied ligamentum flavum by removing all or a portion of the hypertrophied ligamentum flavum, a medical practitioner obtains access to a surgical site including the hypertrophied ligamentum flavum in any appropriate manner, such as through incision and retraction of tissues. In particular, an incision is made in the body of a patient and cannula 32 is inserted into the incision with stylet 46 positioned within passageway 44. Stylet 46 is translated relative to cannula 32 in the direction shown by arrow C such that tip 48 extends through opening 38. Stylet 46 is translated in the direction shown by arrow C until tip 48 creates a surgical pathway from the incision to the hypertrophied ligamentum flavum.

Once the surgical pathway is created, stylet 46 may be removed from passageway 44. Cannula 32 is then moved such that the first end of cannula 32 is positioned adjacent the hypertrophied ligamentum flavum. Member 50 is then inserted into passageway 44 and translated relative to cannula 32 in the direction shown by arrow D such that aperture 56 extends through opening 38 and the cutting tip of member 50 and aperture 56 are positioned adjacent the hypertrophied ligamentum flavum. Electrodes 64 may then be activated to emit radio frequency energy to cut and/or destroy tissue and/or nerves. In embodiments of system 30 that include an irrigation source coupled to the second end of member 50, the irrigation source may be used to deliver irrigation fluid through passageway 54 and aperture 56 such that the irrigation fluid cools electrodes 64 and/or irrigates the hypertrophied ligamentum flavum.

Before or after electrodes 64 are activated to cut and/or destroy tissue and/or nerves, member 50 may be translated relative to cannula 32 in the direction shown by arrow D and/or the direction shown by arrow DD such that the cutting tip of member 50 engages the hypertrophied ligamentum flavum to cut tissue from the hypertrophied ligamentum flavum. Member 50 may also be rotated relative to cannula 32 in the direction shown by arrow E or the direction shown by arrow EE such that the cutting tip of member 50 engages the hypertrophied ligamentum flavum to cut tissue from the hypertrophied ligamentum flavum. In some embodiments, member 50 is translated relative to cannula 32 in the direction shown by arrow D and/or the direction shown by arrow DD and rotated relative to cannula 32 in the direction shown by arrow E or the direction shown by arrow EE simultaneously. This allows the cutting tip of member 50 to cut portions of the hypertrophied ligamentum flavum by mechanical force that are not cut by the radio frequency emitted by electrodes 64 and/or the cutting tip of member 50 to cut portions of the hypertrophied ligamentum flavum by mechanical force prior to cutting portions of the hypertrophied ligamentum flavum by the radio frequency emitted by electrodes 64.

In embodiments of system 30 that include a suction source coupled to the second end of member 50, the suction source may create suction through aperture 56 and passageway 54 such that the cut portion(s) of the hypertrophied ligamentum flavum are suctioned through aperture 56 and into passageway 54. It is envisioned that the suctioning of the cut portion(s) of the hypertrophied ligamentum flavum may occur after the portion(s) of the hypertrophied ligamentum flavum are cut by the radio frequency emitted by electrodes 64, translating member 50 relative to cannula 32 in the direction shown by arrow D and/or the direction shown by arrow DD such that the cutting tip of member 50 engages the hypertrophied ligamentum flavum to cut tissue from the hypertrophied ligamentum flavum and/or rotating member 50 relative to cannula 32 in the direction shown by arrow E or the direction shown by arrow EE such that the cutting tip of member 50 engages the hypertrophied ligamentum flavum to cut tissue from the hypertrophied ligamentum flavum. It is further envisioned that the suctioning of the cut portion(s) of the hypertrophied ligamentum flavum may occur simultaneously with cutting the portion(s) of the hypertrophied ligamentum flavum with the radio frequency emitted by electrodes 64, cutting the portion(s) of the hypertrophied ligamentum flavum by translating member 50 relative to cannula 32 in the direction shown by arrow D and/or the direction shown by arrow DD and/or cutting the portion(s) of the hypertrophied ligamentum flavum by rotating member 50 relative to cannula 32 in the direction shown by arrow E or the direction shown by arrow EE. It is contemplated that the suction provided by the suctioning source may also be used to collect any irrigation fluid in or adjacent the hypertrophied ligamentum flavum delivered by the irrigation source.

After the portion(s) of the hypertrophied ligamentum flavum are cut by system 30 and are suctioned into passageway 54, cannula 32 may be removed from the surgical site through the incision.

In one embodiment, the components of system 30 can be made of radiolucent materials such as polymers. Radiomarkers may be included for identification under x-ray, fluoroscopy, CT or other imaging techniques.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto. The embodiments above can also be modified so that some features of one embodiment are used with the features of another embodiment. One skilled in the art may find variations of these preferred embodiments, which, nevertheless, fall within the spirit of the present invention, whose scope is defined by the claims set forth below.

What is claimed is:

1. A device for performing a surgical procedure on an anatomy of a patient, the device comprising:
   an outer hollow member extending along a longitudinal axis between a proximal end and a distal end, the proximal end defining a first opening, and the distal end defining a second opening, the outer hollow member including an Inner surface defining a first passageway between the first opening and the second opening;
   an inner hollow member having a proximal end and a distal end, the inner hollow member movably disposed in the first passageway between the proximal end and the distal end of the first passageway, the inner hollow member including an inner surface defining a second passageway, the inner hollow member further including a cutting tip defined by an aperture at the distal end thereof, wherein the cutting tip includes the aperture having a first portion extending substantially parallel to the longitudinal axis and the cutting tip being configured to cut patient tissue at a surgical site; and
   a stylet configured for removable disposal in the first passageway, the stylet including a tip extending through the second opening, the stylet being configured for insertion through an incision into the patient, and translation into the anatomy of the patient to create an access path to a selected portion of the patient's anatomy;
   wherein the inner hollow member is movable between a first orientation in which the cutting tip is disposed within the first passageway and the inner hollow member has a substantially linear configuration, and a second orientation in which the distal end of the inner hollow member and the cutting tip extend through the second opening and the inner hollow member has an arcuate configuration.

2. A device as recited in claim 1, wherein the cutting tip includes the aperture having a second portion extending substantially perpendicular to the longitudinal axis.

3. A device as recited in claim 2, wherein the aperture of the cutting tip defines a scoop portion.

4. A device as recited in claim 1, wherein the cutting tip is configured to debulk a hypertrophied ligamentum flavum.

5. A device as recited in claim 1, wherein the inner hollow member comprises a super elastic metal.

6. A device as recited in claim 1, wherein the inner hollow member comprises Nitinol.

7. A device as recited in claim 1, wherein the inner hollow member includes at least one electrode configured to emit radio frequency (RF) energy to destroy tissue, the tissue including at least nerve tissue.

8. A device as recited in claim 7, wherein the electrode is positioned adjacent the aperture.

9. A device as recited in claim 7, wherein the electrode is configured to be energized by monopolar RF.

10. A device as recited in claim 7, wherein the electrode is configured to be energized by bipolar RF.

11. A device as recited in claim 1, wherein the cutting tip is configured to cut through a ligamentum flavum of a patient at a thickness less than about 1.5 mm.

12. A device as recited in claim 1, wherein the proximal end of the inner hollow member is coupled to a suction source.

13. A device as recited in claim 1, wherein the proximal end of the inner hollow member is coupled to an irrigation source.

14. A device as recited in claim 1, wherein:
   the first passageway extends substantially parallel to the longitudinal axis and has a substantially uniform diameter; and
   the first and second openings are substantially circular and extend substantially perpendicular to the longitudinal axis.

15. A method for correction of a bone injury in a patient, the method comprising:
   providing a device comprising:
      an outer hollow member extending along a longitudinal axis between a proximal end and a distal end, the proximal end defining a first opening, and the distal end defining a second opening, the outer hollow member including an inner surface defining a first passageway between the first opening and the second opening;
      an inner hollow member having a proximal end and a distal end, the inner hollow member including an inner surface defining a second passageway, a cutting tip at the distal end, the inner hollow member being configured for movable disposal in the first passageway, between the proximal end and the distal end of the first passageway; and
      a stylet configured for removable disposal in the first passageway, the stylet including a tip that extends through the second opening;
   inserting the stylet through an incision in the patient, and translating the stylet into the anatomy of the patient such that the stylet creates an access path to a selected portion of the patient's anatomy;
   removing the stylet from the first passageway;
   inserting the inner hollow member into the first passageway;
   moving the inner hollow member between a first orientation in which the cutting tip is disposed within the first passageway and the inner hollow member has a substantially linear configuration, and a second orientation in which the distal end of the inner hollow member and the cutting tip extend through the second opening and the inner hollow member has an arcuate configuration; and
   utilizing the cutting tip to cut through the selected portion of the patient's anatomy.

16. A method as recited in claim 15, wherein the selected portion of the patient's anatomy is a ligamentum flavum.

17. A method as recited in claim 15, wherein the inner hollow member includes at least one electrode configured to emit radio frequency (RF) energy; and utilizing the cutting tip of the inner member to cut through the selected portion of the patient's anatomy comprises emitting RF energy from the at least one electrode to one of cut and destroy at least a portion of the selected portion of the patient's anatomy.

18. A method as recited in claim 15, wherein the proximal end of the Inner hollow member is coupled to a suction source, and the method further comprises providing suction from the suction source through the proximal end of the inner hollow member and into the second passageway to remove tissue from the selected portion of the patient's anatomy.

19. A method as recited in claim 15, wherein the proximal end of the Inner hollow member is coupled to an irrigation source, and the method further comprises delivering irrigation fluid from the irrigation source through the proximal end of the inner hollow member and through the second passageway to a location adjacent the selected portion of the patient's anatomy.

20. A method as recited in claim 15, wherein cutting through the selected portion of the patient's anatomy comprises utilizing the cutting tip by applying mechanical force to the inner hollow member.

21. A method as recited in claim 15, wherein the inner hollow member comprises a super elastic metal.

22. A surgical system comprising:
an outer hollow member extending along a longitudinal axis between a proximal end and a distal end, the proximal end including a first opening, and the distal end including a second opening, the outer hollow member including an inner surface defining a first passageway between the first opening and the second opening, the first passageway extending substantially parallel to the longitudinal axis;
a stylet removably disposed in the first passageway, the stylet including a tip configured to extend through the second opening and to create an access path to a selected portion of a patient's anatomy; and
an inner hollow member having a proximal end and a distal end, movably disposed in the first passageway after the stylet is removed from the first passageway, the inner hollow member including an inner surface defining a second passageway, the inner member further including a cutting tip at the distal end thereof, the cutting tip having an aperture including a first portion extending substantially parallel to the longitudinal axis and a second portion extending one of substantially perpendicular to the longitudinal axis, transverse to the longitudinal axis, defining an acute angle with respect to the longitudinal axis, and defining an obtuse angle with respect to the longitudinal axis, the aperture defining a scoop portion of the cutting tip, the inner hollow member including at least one electrode positioned adjacent the aperture configured to emit radio frequency (RF) energy adapted to one of cut and destroy tissue, the tissue including at least nerve tissue, the proximal end of the inner hollow member defining a proximal end aperture;
wherein the proximal end aperture is configured to be coupled to at least one of a vacuum source and an irrigation source; and
wherein the inner hollow member is movable between a first orientation in which the cutting tip is disposed within the first passageway and the inner hollow member has a substantially linear configuration and a second orientation in which the distal end of the inner hollow member and the cutting tip extend through the second opening and the inner member has an arcuate configuration.

23. A device for performing a surgical procedure, the device comprising:
an outer hollow member extending along a longitudinal axis between a proximal end and a distal end, the proximal end defining a first opening, and the distal end defining a second opening, the outer hollow member including an inner surface defining a first passageway between the first opening and the second opening;
an inner hollow member having a proximal end and a distal end, the inner hollow member movably disposed in the first passageway between the proximal end and the distal end of the first passageway, the inner hollow member including an inner surface defining a second passageway, the inner hollow member further including a cutting tip, the cutting tip being defined by an aperture at the distal end thereof, the cutting tip being configured to cut patient tissue at a surgical site; and
a stylet movably mounted in the first passageway, the stylet configured to cut an access path through the patient's tissue, the access path dimensioned for insertion therein of the distal end of the inner hollow member;
wherein the inner hollow member is movable between a first orientation in which the cutting tip is disposed within the first passageway and the inner hollow member has a substantially linear configuration, and a second orientation in which the distal end of the inner hollow member and the cutting tip extend through the second opening and the inner hollow member has an arcuate configuration.

24. A device as recited in claim 23, wherein the cutting tip at the distal end of the inner hollow member is configured to cut at least a ligamentum flavum of the patient.

* * * * *

UNITED STATES PATENT AND TRADEMARK OFFICE
CERTIFICATE OF CORRECTION

| | | |
|---|---|---|
| PATENT NO. | : 9,282,988 B2 | Page 1 of 1 |
| APPLICATION NO. | : 13/804473 | |
| DATED | : March 15, 2016 | |
| INVENTOR(S) | : Goshayeshgar | |

It is certified that error appears in the above-identified patent and that said Letters Patent is hereby corrected as shown below:

On the Title Page, in Item (71), under "Applicant", in Column 1, Line 1, delete "SÁRL, Neuchatel" and insert -- SÀRL, Neuchâtel --, therefor.

In the Specification

In Column 4, Line 37, delete "stylet" and insert -- stylet to --, therefor.

In Column 6, Line 42, delete "polyaetide," and insert -- polyketide, --, therefor.

In Column 6, Line 43, delete "polycaroplaetohe" and insert -- polycaprolactone --, therefor.

In Column 8, Line 63, delete "impedence-based" and insert -- impedance-based --, therefor.

In the Claims

In Column 11, Line 32, in Claim 1, delete "Inner" and insert -- inner --, therefor.

In Column 13, Line 7, in Claim 18, delete "Inner" and insert -- inner --, therefor.

In Column 13, Line 13, in Claim 19, delete "Inner" and insert -- inner --, therefor.

Signed and Sealed this
Seventeenth Day of May, 2016

Michelle K. Lee
*Director of the United States Patent and Trademark Office*